United States Patent
Cha et al.

(10) Patent No.: US 11,684,694 B2
(45) Date of Patent: Jun. 27, 2023

(54) THERMOSENSITIVE CHITOSAN HYDROGEL COMPOSITION AND BIOINK COMPOSITION COMPRISING THE SAME

(71) Applicant: MEDIFAB CO., LTD., Seoul (KR)

(72) Inventors: Mi Sun Cha, Seoul (KR); Jung Ju Kim, Ansan-si (KR)

(73) Assignee: MEDIFAB CO., LTD., Seoul (KR)

( * ) Notice: Subject to any disclaimer, the term of this patent is extended or adjusted under 35 U.S.C. 154(b) by 0 days.

(21) Appl. No.: 17/253,064

(22) PCT Filed: Apr. 24, 2020

(86) PCT No.: PCT/KR2020/005440
§ 371 (c)(1),
(2) Date: Dec. 16, 2020

(87) PCT Pub. No.: WO2020/262817
PCT Pub. Date: Dec. 30, 2020

(65) Prior Publication Data
US 2022/0202989 A1    Jun. 30, 2022

(30) Foreign Application Priority Data

Jun. 27, 2019  (KR) .................. 10-2019-0077251

(51) Int. Cl.
*A61L 27/20*   (2006.01)
*B33Y 10/00*   (2015.01)
(Continued)

(52) U.S. Cl.
CPC .............. *A61L 27/20* (2013.01); *A61L 27/12* (2013.01); *A61L 27/222* (2013.01); *A61L 27/26* (2013.01);
(Continued)

(58) Field of Classification Search
CPC .................................. A61L 27/20; A61L 27/52
See application file for complete search history.

(56) References Cited

U.S. PATENT DOCUMENTS

| | | | |
|---|---|---|---|
| 6,344,488 B1 | 2/2002 | Chenite et al. | |
| 2014/0335056 A1 | 11/2014 | Chiou et al. | |
| 2019/0054015 A1 | 2/2019 | Kim et al. | |

FOREIGN PATENT DOCUMENTS

| | | | |
|---|---|---|---|
| CN | 1593385 A | * | 3/2005 |
| CN | 1593385 A |   | 3/2005 |

(Continued)

OTHER PUBLICATIONS

Douglas et al Enrichment of Thermosensitive Chitosan Hydrogens with Glycerol and Alkaline Phosphatase for Bone Tissue Engineering Applications, Acta of Bioengineering and Biomechanics, vol. 18, No. 2, pp. 51-57. (Year: 2016).*

(Continued)

*Primary Examiner* — Carlos A Azpuru
(74) *Attorney, Agent, or Firm* — Fitch, Even, Tabin & Flannery LLP (57) ABSTRACT

Provided is a chitosan hydrogel composition including chitosan, glycerol, and a phosphate group, wherein the chitosan is crosslinked via the glycerol, the phosphate group, or a combination thereof. The temperature at which the chitosan hydrogel composition may be induced from a liquid state into a gel state may be controlled according to the content ratio of the phosphate group and the glycerol, and since printing properties and strength are affected by the gelatin concentration, the composition may be used as an ink for 3D printing.

10 Claims, 8 Drawing Sheets

(51) Int. Cl.
*B33Y 70/00* (2020.01)
*B33Y 80/00* (2015.01)
*B29C 64/106* (2017.01)
*A61L 27/12* (2006.01)
*A61L 27/22* (2006.01)
*A61L 27/26* (2006.01)
*A61L 27/52* (2006.01)

(52) U.S. Cl.
CPC ............ *A61L 27/52* (2013.01); *B29C 64/106* (2017.08); *B33Y 10/00* (2014.12); *B33Y 70/00* (2014.12); *B33Y 80/00* (2014.12); *A61L 2430/34* (2013.01)

(56) References Cited

FOREIGN PATENT DOCUMENTS

| CN | 101148520 A | 3/2008 |
| CN | 108697805 A | 10/2018 |
| KR | 10-2018-0117417 A | 10/2018 |
| KR | 2018-0117417 A * | 10/2018 |

OTHER PUBLICATIONS

Owczarz et al (Injectable Chitosan Scaffold with Calcium Beta-Glycerophosphate as the Only Neutralizing Agent, Processes, pp. 1-18, vol. 7, No. 297). (Year: 2019).*

Kim et al, An Electrostatically Crosslinked Chitosan Hydrogel as a Drug Carrier, Molecules, 17, 13704-13711 (Year: 2012).*

KIPO, Application No. PCT/KR2020/005440; International Search Report dated Jul. 31, 2020.

Croisier, Florence et al. "Chitosan-based biomaterials for tissue engineering," European Polymer Journal, 2013, pp. 780-792, vol. 49.

Cheng, Yung-Hsin et al., "Thermosensitive Chitosan-Gelatin-Glycerol Phosphate Hydrogels as a Cell Carrier for Nucleus Pulposus Regeneration: An In Vitro Study," Tissue Engineering, 2010, pp. 695-703, vol. 16. No. 2.

Chenite, A et al. "Novel injectable neutral solutions of chitosan form biodegradable gels in situ," Biomaterials 21, 2000, pp. 2155-2161.

Owczarz, Piotr et al. , "Injectable Chitosan Scaffolds with Calcium b-Glycerophosphate as the Only Neutralizing Agent," Processes, May 19, 2019, pp. 1-18, vol. 7, No. 297.

CNIPA; Application No. 202080005995.4; Office Action dated Sep. 8, 2021.

Timothy E.L. Douglas et al., "Enrichment of thermosensitive chitosan hydrogels with glycerol and alkaline phosphatase for bone tissue engineering applications," Acta of Bioengineering and Biomechanics, vol. 18, No. 2, pp. 51-57, Dec. 31, 2016.

Becerra, José, et al., Demineralized Bone Matrix Mediates Differentiation of Bone Marrow Stromal Cells In Vitro: Effect of Age of Cell Donor, Journal of Bone and Mineral Research, vol. 11, No. 11, 1996, pp. 1703-1714.

Persson, Maria, et al., Osteogenic Differentiation of Human Mesenchymal Stem Cells in a 3D Woven Scaffold, Scientific Reports, 2018, 8:10457, pp. 1-12.

* cited by examiner

THERMOSENSITIVE CHITOSAN HYDROGEL COMPOSITION AND BIOINK COMPOSITION COMPRISING THE SAME

CROSS-REFERENCE TO RELATED APPLICATIONS

This application is a U.S. national phase application filed under 35 U.S.C. § 371 of International Application No. PCT/KR2020/005440, filed Apr. 24, 2020 which is based upon and claims the benefit of priority from the prior Korean Application No. 10-2019-0077251, filed Jun. 27, 2019.

FIELD

The present disclosure relates to a thermosensitive chitosan hydrogel composition and a bioink composition including the same.

BACKGROUND 3D bioprinting, which is one of the 3D printing technologies, is a technology for producing tissues or organs by arranging living cells in a desired structure and pattern. Currently, in skin, organ, or bone transplantation, donations are mostly used. It is difficult to find suitable tissues or organs for transplantation, and even when they are transplanted, there are many problems due to autoimmune responses. To overcome these problems, studies have been actively conducted in the fields of tissue engineering and scaffolds to produce various artificial substitutes such as artificial bones, dental prostheses, artificial blood vessels, artificial skin, artificial organs, and biochips using biodegradable and biocompatible polymeric materials.

Meanwhile, natural polymers such as gelatin, chitosan, collagen, hyaluronic acid, alginate, etc. may be used for 3D bioprinting because they are easy to process and shape and have high biocompatibility, and when introduced into the human body, most of them have good physiological activity and cell adhesion, and rarely cause immune responses. However, the polymers have a disadvantage in that it is difficult to control their decomposition rate because they are easily degraded by heat due to low heat resistance and are rapidly decomposed in the body due to low mechanical properties.

SUMMARY

Accordingly, there is a need to develop a naturally derived polymer capable of controlling temperature sensitivity according to the type and content of a crosslinking agent.

An aspect of the present disclosure is to provide a chitosan hydrogel composition including chitosan, glycerol, and a phosphate group, wherein the chitosan is crosslinked via the glycerol, the phosphate group, or a combination thereof.

Another aspect of the present disclosure is to provide a bioink composition including the hydrogel composition.

A chitosan hydrogel composition according to an aspect employs a phosphate group and glycerol as crosslinking agents, and thus it may be a substitute for beta-glycerophosphate (β-glycerophosphate) playing a role in cell responses while maintaining cellular features. Further, the temperature at which the composition may be induced from a liquid state into a gel state may be controlled according to the content ratio of the phosphate group and the glycerol, and since printing properties and strength are affected by the gelatin concentration, the composition may be used as an ink for 3D printing. Furthermore, the chitosan hydrogel composition may be used as a casting ink by acting as a crosslinker between different types of hydrogels.

DETAILED DESCRIPTION

An aspect provides a chitosan hydrogel composition including chitosan, glycerol, and a phosphate group, wherein the chitosan is crosslinked via the glycerol, the phosphate group, or a combination thereof. Another aspect provides a bioink composition including the hydrogel composition. The ink composition may be a casting ink composition.

As used herein, the term "hydrogel" may refer to a three-dimensional network structure made by crosslinking hydrophilic polymers through covalent or non-covalent bonding. Due to hydrophilicity of components, hydrogel absorbs a large amount of water to swell in an aqueous solution or under an aqueous environment, but is not dissolved due to the crosslinked structure. Therefore, hydrogels having various shapes and properties may be made depending on components and preparation methods, and hydrogels generally contain a large amount of water, and thus they may be intermediate in their properties between liquids and solids.

As used herein, the term "bioink" may refer to hydrogel, a mixture of hydrogel and cells, or a mixture of hydrogel and physiologically active materials, which is used for bioprinting. Therefore, the bioink composition may be for bioprinting. Further, the bioink composition may be a hydrogel. More particularly, the bioink composition may be used as a material for the production of a scaffold for tissue regeneration, a patient-customized scaffold, or for the development of tissues and artificial organs to replace animal tests, etc. Specifically, the scaffold for tissue regeneration may be mixed with biomaterials, such as cells, growth factors, etc., to produce skin, cornea, bone, cartilage, blood vessels, etc.

As used herein, the term "casting ink" refers to a hydrogel ink including a crosslinking agent capable of serving as a crosslinker between hydrogels with weak physical properties. The crosslinking agent is not limited to its kind, such as chemical crosslinking agents, natural crosslinking agents, etc. For example, the crosslinking agent may be β-glycerophosphate (β-GP), glucose 1-phosphate (G1-P), etc. Specifically, when the casting ink is printed between bioinks, it plays a role in stably gelling the bioinks by the crosslinking agent included in the casting ink during the printing process, and also plays a role in more stably maintaining the complex structure and shape of the printed scaffold.

As used herein, the term "chitosan" may refer to a linear polysaccharide consisting of D-glucosamine and N-acetyl glucosamine. The chitosan may be represented by the following structural formula 1 and may be obtained by treating crab, shrimp, and crustacean shells with a sodium hydroxide base, but is not limited thereto. The chitosan may include chitosan derivatives, in addition to pure chitosan. For example, the chitosan derivatives may include at least any one of phthalated chitosan, esterified chitosan, amidated chitosan, or formylated chitosan:

[Structural Formula 1]

As used herein, the term "gelatin" may refer to a protein obtained by partial hydrolysis of collagen, which is a major protein component of connective tissues, such as bones, cartilages, and leathers of animals. The gelatin may include gelatin derivatives, in addition to pure gelatin. For example, the gelatin derivatives may include at least any one of phthalated gelatin, esterified gelatin, amidated gelatin, or formylated gelatin. With regard to the gelatin, its kind (source) is not particularly limited, and for example, various gelatins derived from mammals, fish, such as cow bone, cow skin, pig bone, pig skin, etc., may be used. Further, the gelatin may have a molecular weight of 40,000 to 100,000, 40,000 to 80,000, or 60,000 to 80,000. Further, the gelatin may have a molecular weight of 100,000 to 250,000, 120,000 to 240,000, or 150,000 to 200,000.

Figure 1:
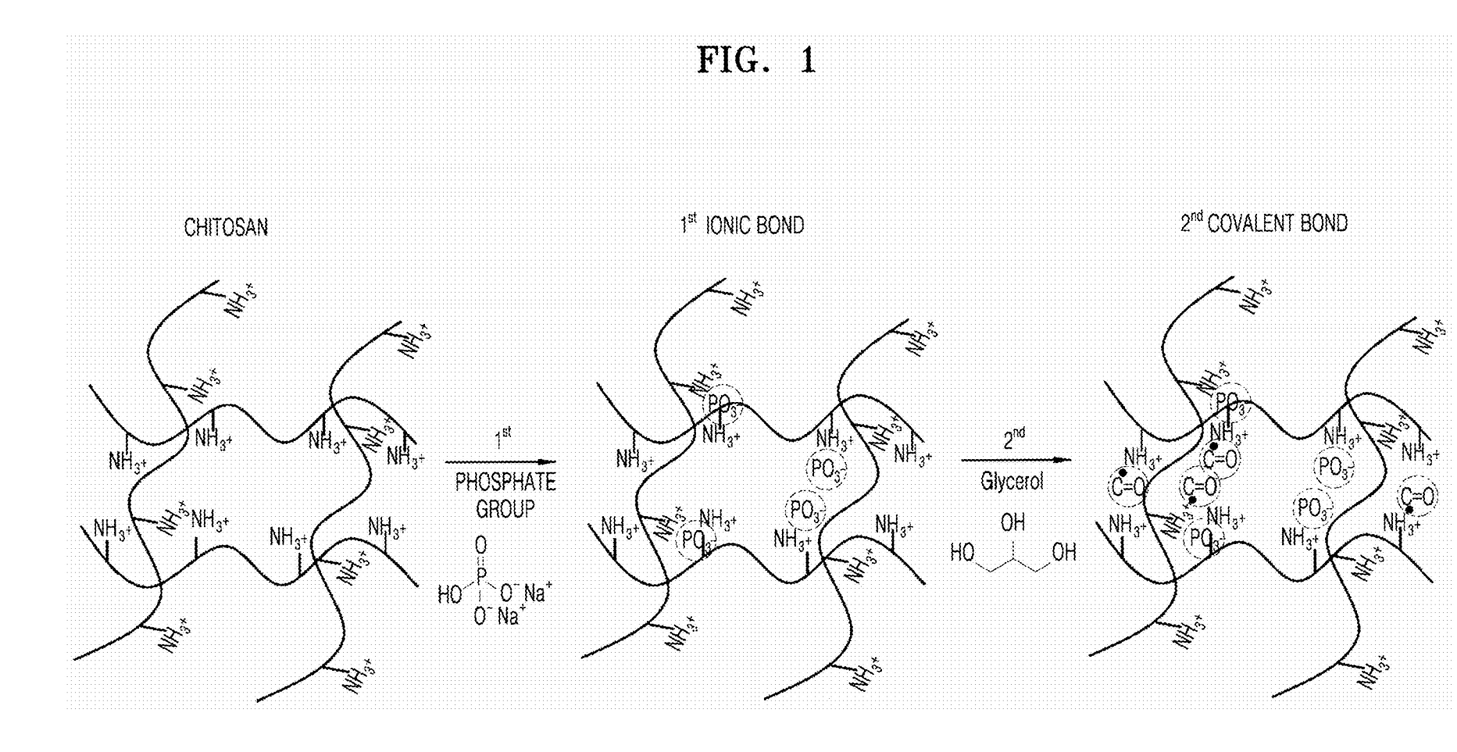
FIG. 1 shows an illustration of crosslinking properties of a thermosensitive chitosan hydrogel according to one aspect.

The composition according to one aspect may include chitosan, glycerol, and a phosphate group, wherein the chitosan is crosslinked by the glycerol, the phosphate group, or a combination thereof. With regard to the chitosan, a first chitosan and a second chitosan may be crosslinked by the glycerol, the phosphate group, or a combination thereof to form a chitosan polymer. The crosslinking may be covalent linking or non-covalent linking. FIG. 1 shows an illustration of crosslinking properties of a thermosensitive chitosan hydrogel according to one aspect. In a specific embodiment, the first chitosan and the second chitosan may form covalent bonding by the glycerol. In another specific embodiment, the first chitosan and the second chitosan may form non-covalent bonding by the phosphate group. Therefore, the chitosan polymer may include both of the non-covalent bonding with the phosphate group and the covalent bonding with the glycerol. In other words, in the chitosan hydrogel composition according to one aspect, the first chitosan and the second chitosan may form the covalent bonding and/or non-covalent bonding by the glycerol and/or the phosphate group, and thus the strength of the composition may be controlled by controlling the kind and content of the crosslinking agent. The glycerol and the phosphate group may be included at a molar ratio of 1:10 to 10:1. For example, they may be included at a molar ratio of 1:10 to 10:1, 1:8 to 8:1, 1:5 to 5:1, 2:7 to 7:2, 3:6 to 6:3, 2.5:7.5 to 7.5:2.5, 4:5 to 5:4, or 1:4 to 1:1. In this regard, when the ratio of the glycerol and the phosphate group is less than the above range, physical property of the gelled ink becomes weak, and thus it is difficult to make a laminated structure, and it is difficult to achieve 3D printing and complex structures. When the ratio is more than the above range, there is a problem in that when cells or growth factors are mixed with the materials, they may exhibit cytotoxicity or may affect proliferation and differentiation. In other words, the chitosan polymer may control the binding strength of chitosan molecules by controlling the content of the glycerol and the phosphate group. In addition, the glycerol and the phosphate group may be included in the composition in an amount of 1% by weight to 30% by weight, based on the total weight of the composition. For example, the glycerol and the phosphate group may be included in the composition in an amount of 1% by weight to 30% by weight, 2% by weight to 20% by weight, 2% by weight to 18% by weight, 2% by weight to 15% by weight, 2% by weight to 9% by weight, 5% by weight to 18% by weight, 5% by weight to 15% by weight, 8% by weight to 19% by weight, 12% by weight to 18% by weight or 16% by weight to 19% by weight, based on the total weight of the composition. In this regard, when the content of the glycerol and the phosphate group is less than the above range, the composition is not gelled or the physical property after gelation becomes weak, and thus it is difficult to make a laminated structure. Therefore, there is a problem in that it is not suitable for 3D printing. When the composition is mixed with cells, there is a problem in that 3D culture is difficult due to rapid decomposition. In addition, when the content of the glycerol and the phosphate group is more than the above range, there is a problem in that gelation of the composition rapidly occurs, resulting in increased viscosity during printing of cells or growth factors, and thus it is difficult to control a pneumatic pressure.

The chitosan may be deacetylated.

In a specific embodiment, gelation of the composition may occur at 15° C. to 60° C. For example, the temperature at which the gelation occurs may be 15° C. to 60° C., 15° C. to 57° C., 20° C. to 57° C., 20° C. to 50° C., 20° C. to 45° C., 37° C. to 57° C., or 30° C. to 45° C. In this regard, when the temperature at which the gelation occurs is lower than the above range, there is a problem in that gelation does not occur, or the composition is hardened by gelatin before crosslinking formation. When the temperature is higher than the above range, there is a problem in that gelation of the composition proceeds faster than a desired time. Further, gelation of the composition may occur within 10 minutes to 30 hours. For example, the time at which gelation occurs may be 10 minutes to 30 hours, 10 minutes to 24 hours, 30 minutes to 20 hours, 30 minutes to 16 hours, 1 hour to 12 hours, 3 hours to 8 hours, or 10 hours to 30 hours. In this regard, when the time at which the gelation occurs is shorter than the above range, there is a problem in that the gelation does not occur, or crosslinking partially forms, and thus the composition is produced in an unstable form. When the time is longer than the above range, there is a problem in that no phase transition occurs unless the temperature is changed. The composition may have pH of 6.6 to 6.9. For example, the composition may have pH of 6.6 to 6.9, 6.6 to 6.8, 6.6 to 6.7, or 6.7 to 6.8. In this regard, when the pH is lower than the above range, there is a problem in that gelation does not occur even though the temperature or time is changed, and when the pH is higher than the range, gelation occurs during addition of the crosslinking agent, and thus it is difficult to use the composition as a thermosensitive bioink.

In one embodiment, the composition may further include gelatin. The gelatin may influence printing properties and strength for using the composition as a bioink. Specifically, the gelatin may be included in the composition in an amount of 0.1% by weight to 10% by weight, based on the total weight of the composition. For example, the gelatin may be included in the composition in an amount of 0.1% by weight to 10% by weight, 0.5% by weight to 8% by weight, 0.5% by weight to 6% by weight, 1% by weight to 5% by weight, 2% by weight to 5% by weight, 2% by weight to 4.5% by weight, or 3.5% by weight to 4.5% by weight, based on the total weight of the composition. In this regard, when the content of gelatin is less than the above range, there is a problem in that cell compatibility such as cell adhesion or proliferation is poor, and thus its applicability as a bioink may decrease. When the content of gelatin is more than the above range, there is a problem in that the strength of the bioink may be lowered, and gelation may not occur well due to the reduced relative content of chitosan, which plays a role in crosslinking.

The composition may be used as a casting ink by further including a salt. For example, the composition may further include calcium chloride, calcium sulfate, calcium carbonate, barium chloride, barium sulfate or a combination thereof. In other words, by further including the salt, strength of the ink is increased upon cross-laminating with the bioink, and thus there is an advantage in that it is possible to print in a multilayer structure, and the laminated form may be maintained even after printing.

Hereinafter, preferred exemplary embodiments will be provided for better understanding of the present disclosure. However, the following exemplary embodiments are provided only for understanding the present disclosure more easily, but the content of the present disclosure is not limited to the following exemplary embodiments.

EXAMPLE

Example 1

Figure 2A:
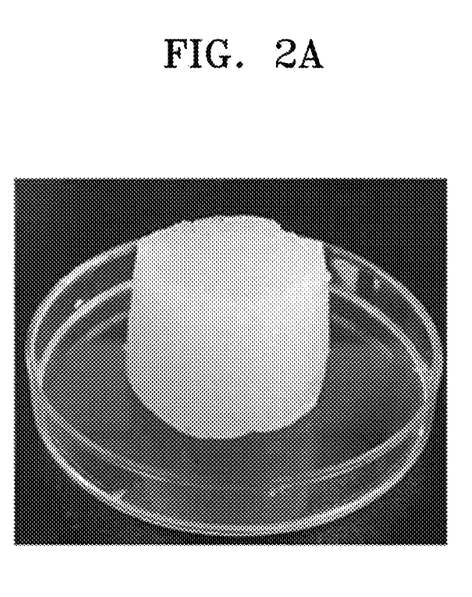
FIG. 2A shows a photograph of a chitosan hydrogel prepared in Example 1.

0.675 g of gelatin was added to 15 ml of 0.1 N HCL, and stirred at 60° C. for 1 hour at 500 rpm to prepare a gelatin solution. Thereafter, 0.6 g of chitosan was added to the gelatin solution, and then 0.3 ml of a mixed solution of 0.5 M disodium phosphate ($Na_2HPO_4$) and 0.5 M glycerol was slowly dropped and pH thereof was adjusted to 7. Then, the solution was stored at 57° C. for 1 day, and gelation was observed (FIG. 2A).

Example 2

Figure 2B:
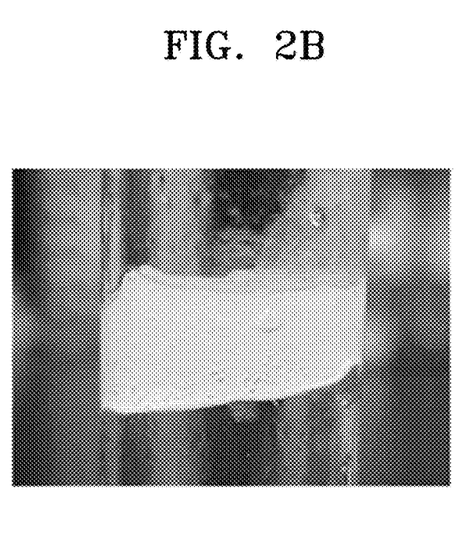
FIG. 2B shows a photograph of a chitosan hydrogel prepared in Example 2.

0.25 g of gelatin was added to 10 ml of 0.1 N HCL, and stirred at 60° C. for 1 hour at 500 rpm to prepare a gelatin solution. Thereafter, 0.3 g of chitosan was added to the gelatin solution, and then a mixed solution of 0.5 M disodium phosphate ($Na_2HPO_4$) and 0.5 M glycerol was slowly dropped and pH thereof was adjusted to 6.8. Then, the solution was stored at 57° C. for 10 minutes, and gelation was observed (FIG. 2B).

Example 3

Figure 2C:
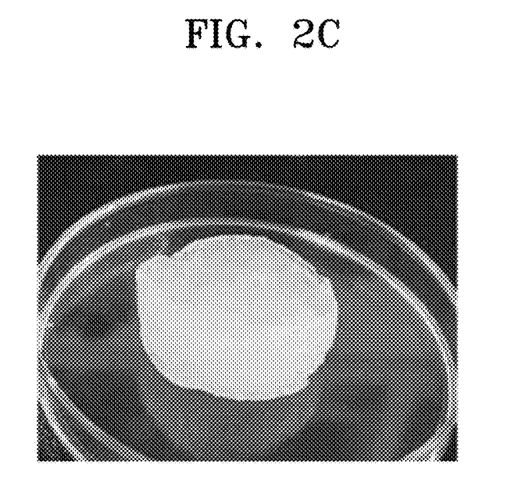
FIG. 2C shows a photograph of a chitosan hydrogel prepared in Example 3.

0.35 g of gelatin was added to 10 ml of 0.1 N HCL, and stirred at 60° C. for 1 hour at 500 rpm to prepare a gelatin solution. Thereafter, 0.3 g of chitosan was added to the gelatin solution, and stirred at 2000 rpm for 4 hours, and then a mixed solution of 0.5 M disodium phosphate ($Na_2HPO_4$) and 0.5 M glycerol was slowly dropped and pH thereof was adjusted to 6.8. Then, the solution was stored at room temperature for 1 day, and gelation was observed (FIG. 2C).

Example 4

Figure 2D:
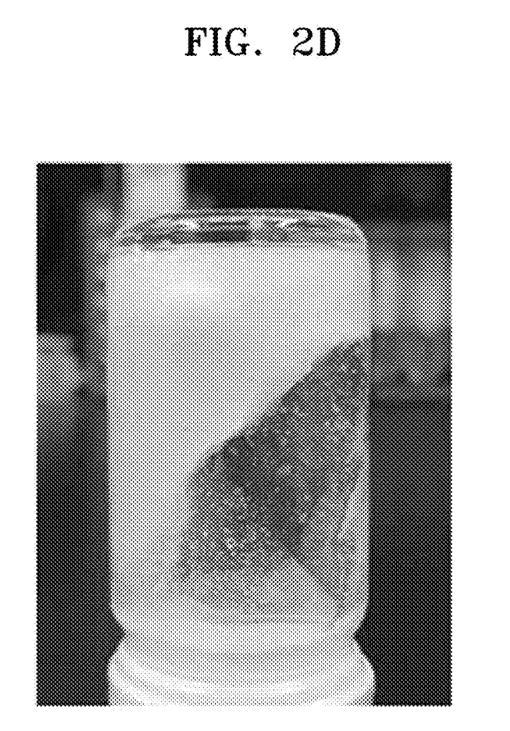
FIG. 2D shows a photograph of a chitosan hydrogel prepared in Example 4.

0.2 g of gelatin was added to 10 ml of 0.1 N HCL, and stirred at 60° C. for 1 hour at 500 rpm to prepare a gelatin solution. Thereafter, 0.25 g of chitosan was added to the gelatin solution, and stirred at 2000 rpm for 4 hours, and then a mixed solution of 0.5 M disodium phosphate ($Na_2HPO_4$) and 0.5 M glycerol was slowly dropped and pH thereof was adjusted to 6.8. Then, the solution was stored at room temperature for 1 day, and gelation was observed (FIG. 2D).

Example 5

Figure 2E:
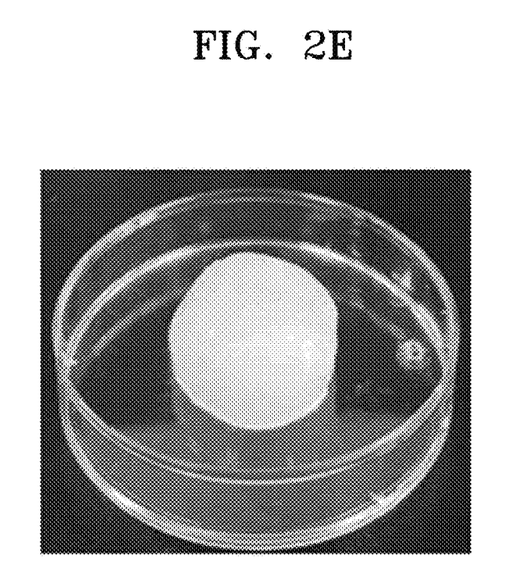
FIG. 2E shows a photograph of a chitosan hydrogel prepared in Example 5.

0.2 g of gelatin was added to 10 ml of 0.1 N HCL, and stirred at 60° C. for 1 hour at 500 rpm to prepare a gelatin solution. Thereafter, 0.25 g of chitosan was added to the gelatin solution, and stirred at 2000 rpm for 4 hours, and then a mixed solution of 0.5 M disodium phosphate ($Na_2HPO_4$) and 2 M glycerol was slowly dropped and pH thereof was adjusted to 6.5. Then, the solution was stored at 37° C. for 1 hour, and gelation was observed (FIG. 2E).

Example 6

Figure 2F:
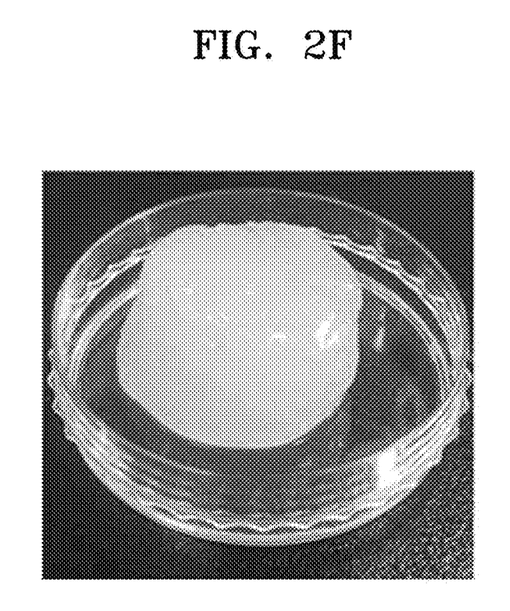
FIG. 2F shows a photograph of a chitosan hydrogel prepared in Example 6.

0.2 g of gelatin was added to 10 ml of 0.1 N HCL, and stirred at 60° C. for 1 hour at 500 rpm to prepare a gelatin solution. Thereafter, 0.25 g of chitosan was added to the gelatin solution, and stirred at 2000 rpm for 4 hours, and then 1.34 ml of a mixed solution of 1 M disodium phosphate ($Na_2HPO_4$) and 4 M glycerol was slowly dropped and pH thereof was adjusted to 6.5. Then, the solution was stored at 37° C. for 30 minutes, and gelation was observed (FIG. 2F).

Example 7

0.525 g of gelatin was added to 15 ml of 0.1 N HCL, and stirred at 60° C. for 20 minutes at 800 rpm to prepare a gelatin solution. Thereafter, 0.45 g of chitosan was added to the gelatin solution, and stirred at 2000 rpm for 4 hours, and then a mixed solution of 1 M disodium phosphate ($Na_2HPO_4$) and 4 M glycerol was slowly dropped and pH thereof was adjusted to 7.1. Then, the solution was stored at 4° C. for 1 day, and gelation was observed.

EXPERIMENTAL EXAMPLE

Experimental Example 1. Examination of Cell Adhesion and Cytotoxicity of Chitosan Hydrogel The chitosan hydrogel prepared in Example 5 was prepared into a 24-well-sized membrane, followed by gelation. In detail, 500 μl of Example 5 was added to each of 24 wells, followed by gelation at 37° C. for 1 hour. Thereafter, Raw and E1 cells were dispensed to the gel at a density of $1\times10^4$ cells/well, respectively. 4 hours later, cell adhesion was observed. On day 1, day 2, and day 3, reaction was allowed by a WST method for 2 hours to examine absorbance, and thus cell proliferation was examined, respectively.

Figure 3A:
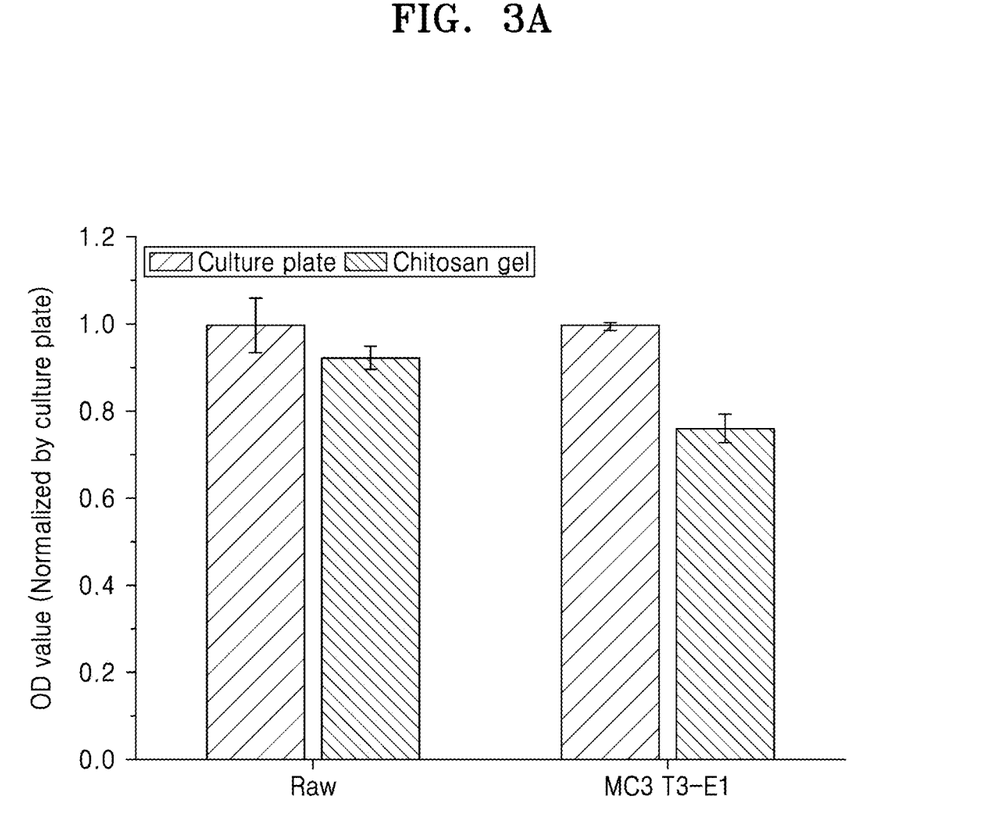
FIG. 3A shows a graph showing cell adhesion of cells dispensed in the chitosan hydrogel prepared in Example 5.
Figure 3B:
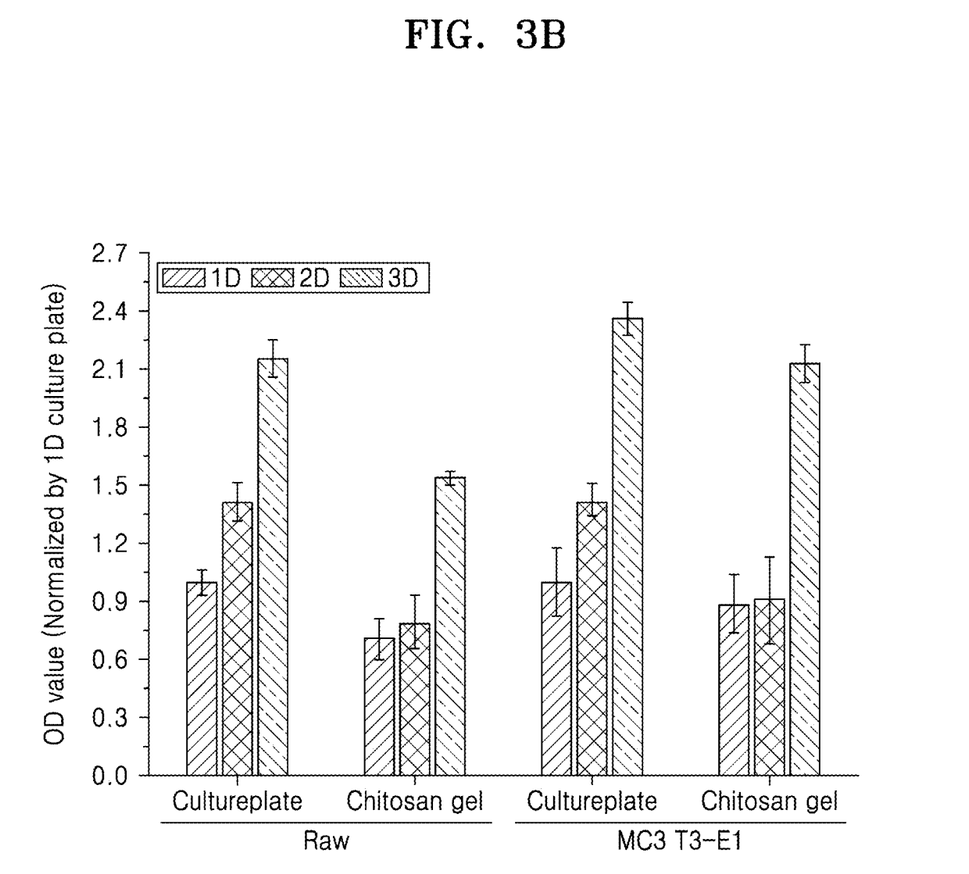
FIG. 3B shows a graph showing cell proliferation of cells cultured in the chitosan hydrogel prepared in Example 5.

FIG. 3A shows a graph of OD values representing adhesion of cells dispensed to Example 5, and FIG. 3B shows a graph of OV values representing proliferation of cells cultured in Example 5.

As shown in FIG. 3A, cells dispensed to the chitosan gel showed significantly low adhesion, as compared with the control group. In detail, with regard to cell adhesion, as absorbance of the control group was regarded as 1 (100%), Raw cells and E1 cells dispensed to the chitosan gel showed absorbance of 0.92 (92%) and 0.76 (76%), respectively. With regard to cell proliferation, as absorbance of the control group was regarded as 1 (100%), Raw cells and E1 cells dispensed to the chitosan gel showed absorbance of 0.71 (71%) and 0.89 (89%), respectively. That is, as shown in FIG. 3B, proliferation of cells cultured in the chitosan hydrogel significantly increased over time, indicating a remarkably increased cell proliferation rate, as compared with that of cells cultured in the control group. In other words, the chitosan hydrogel according to one aspect maintained 70% to 80% or more of cell adhesion and proliferation, as compared with the control group.

Experimental Example 2. Examination of Printing Properties of Chitosan Gel 3D printing properties of the chitosan hydrogel prepared in Example 7 was examined. In detail, a 10 ml luer lock syringe (BD) was filled with an appropriate amount of 1 ml to 5 ml of the chitosan hydrogel, followed by gelation at 4° C. for 20 minutes to 30 minutes. The syringe in which gelation occurred was fixed in an extruder. At this time, to prevent changes in physical properties during the printing process, the internal temperature in the printer was maintained at 4° C. The printing sample was 3D-molded to 10×10×2 (mm) of a hollow shape without ceiling and floor surface, and optimal printing conditions were set. As for setting values, the layer height was set to 0.1 mm (thickness of one layer of laminated layers), and the nozzle size was set to 0.21 mm, and thus the conditions were similar to those of a 25 G needle (about 0.241 mm). In addition, the square infill was 20% to 25%, and an appropriate mesh was formed inside, and the printing speed was set to 10 mm/sec. The pressure during printing was set to psi 45 to psi 55.

Figure 4:
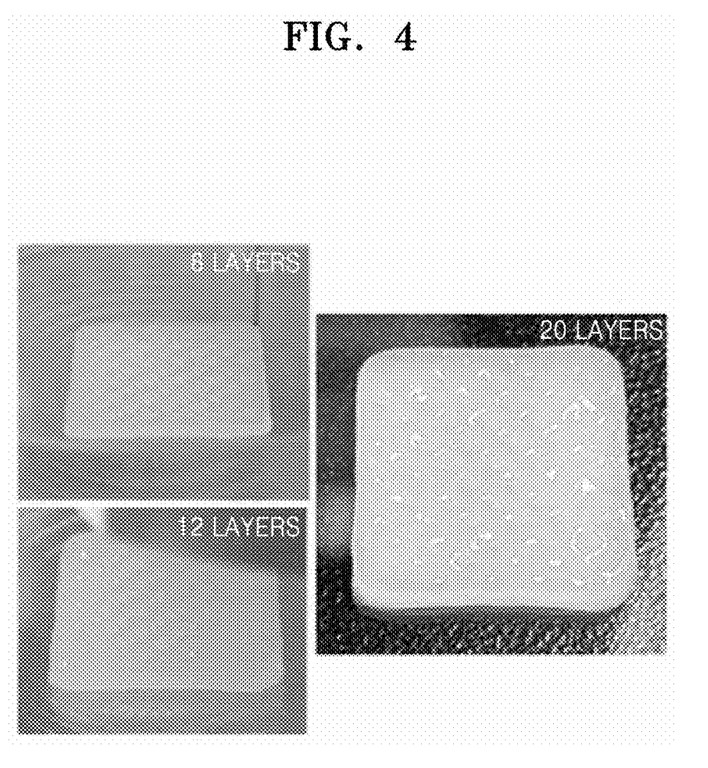
FIG. 4 shows photographs showing 3D bioprinting properties of the chitosan hydrogel prepared in Example 7.

FIG. 4 shows photographs showing 3D bioprinting properties of the chitosan hydrogel. As shown in FIG. 4, it was confirmed that the chitosan hydrogel according to one aspect may be stacked up to 20 layers regardless of changes in the size or shape to be printed. Accordingly, the chitosan hydrogel according to one aspect overcomes the disadvantage of general hydrogels, in which it is difficult to stack up to high layers due to weak physical property, and thus it may be used as an ink for 3D printing.

Experimental Example 3. Examination of Applicability of Chitosan Gel to Casting Ink When different types of hydrogels are printed, a crosslinking agent or a material acting as a crosslinker is printed on the bottom layer, and in this case, it is difficult to form a uniform expression. For this reason, there is a disadvantage in that the shape of the printing product is not uniform, and cytotoxicity may be caused by a crosslinking agent or the scaffold may collapse. Therefore, to examine applicability of the chitosan hydrogel according to one aspect as a casting ink, a laminated structure of a chitosan hydrogel and a bioink was manufactured.

First, the chitosan hydrogel ink was prepared. In detail, 0.2 g of gelatin was added to 10 ml of 0.1 N HCl and stirred at 60° C. for 1 hour at 500 rpm to prepare a gelatin solution. Then, 0.147 g of $CaCl_2$ was added thereto. Thereafter, 0.25 g of chitosan was added to the gelatin solution, and stirred at 2000 rpm for 4 hours. Then, the solution was stored at 4° C. for 30 minutes to observe gelation. Next, the bioink was prepared. In detail, 0.5 ml of glycerol was added to 10 ml of PBS and stirred at 300 rpm for 5 minutes. Then, 0.25 g of dextran 40 was added and stirred at 300 rpm for 5 minutes. Thereafter, 0.5 g of gelatin was added and stirred at 60° C. and 500 rpm for 15 minutes. 0.3 g of alginate was added thereto and stirred at 60° C. and 500 rpm for 40 minutes and gelation was allowed at 4° C. for 20 minutes to 30 minutes. Thereafter, the chitosan hydrogel was dual-printed into four layers with a layer height of 0.1 mm and a nozzle diameter of 25 G (0.241 mm) at a print speed of 10 mm/s, and the bioink was printed into four layers under the same conditions, and then four layers of chitosan hydrogel were additionally printed. It was confirmed that the chitosan hydrogel; a laminated structure of the bioink and the chitosan hydrogel were gelled. The gelled printing product was stored at 4° C. for 1 day, and then was put in 1 ml of PBS to examine whether the gel was maintained.

Figure 5:
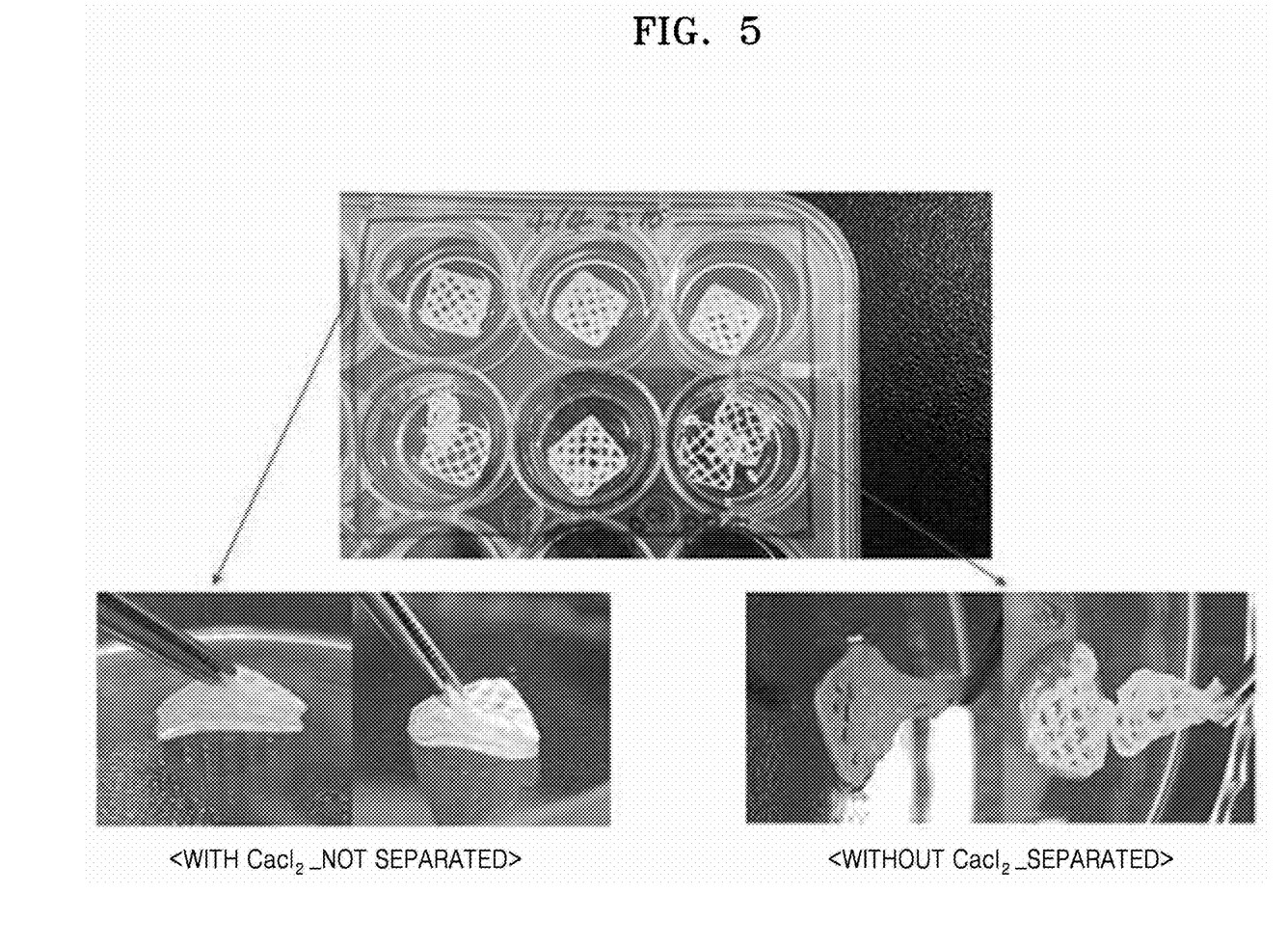
FIG. 5 shows photographs showing applicability of the chitosan hydrogel according to one aspect as a casting ink.

FIG. 5 shows photographs showing applicability of the chitosan hydrogel as a casting ink. As shown in FIG. 5, it was confirmed that the chitosan hydrogel with $CaCl_2$) maintained the laminated structure without separation from the biogel, whereas the chitosan hydrogel without $CaCl_2$) was separated from the biogel. In other words, the chitosan hydrogel according to one aspect may be applied as a casting ink by further including $CaCl_2$).

The invention claimed is:

1. A chitosan hydrogel composition comprising chitosan, glycerol, and a phosphate group, wherein the chitosan comprises a first chitosan and a second chitosan crosslinked with each other,
    wherein the glycerol and phosphate group are used as crosslinking agents,
    wherein the glycerol and the phosphate group are comprised at a molar ratio of 1:1 to 1:4,
    wherein gelation of the composition occurs at 15° C. to 60° C., and
    wherein the composition forms a laminated structure when used as an ink for 3D printing.

2. The chitosan hydrogel composition of claim 1, wherein the first chitosan and the second chitosan are crosslinked via covalent bonding or non-covalent bonding.

3. The chitosan hydrogel composition of claim 2, wherein the covalent bonding is formed by crosslinking of the first chitosan and the second chitosan via the glycerol.

4. The chitosan hydrogel composition of claim 2, wherein the non-covalent bonding is formed by crosslinking of the first chitosan and the second chitosan via the phosphate group.

5. The chitosan hydrogel composition of claim 1, wherein gelation of the composition occurs within 10 minutes to 30 hours.

6. The chitosan hydrogel composition of claim 1, wherein pH of the composition is 6.6 to 6.9.

7. The chitosan hydrogel composition of claim 1, wherein the glycerol and the phosphate group are comprised in the composition in an amount of 1% by weight to 30% by weight, based on the total weight of the composition.

8. The chitosan hydrogel composition of claim 1, further comprising gelatin.

9. The chitosan hydrogel composition of claim 1, wherein the gelatin is comprised in the composition in an amount of 0.1% by weight to 10% by weight, based on the total weight of the composition.

10. The chitosan hydrogel composition of claim 1, further comprising a salt selected from the group consisting of calcium chloride, calcium sulfate, calcium carbonate, barium chloride, and barium sulfate.

\* \* \* \* \*